(12) United States Patent
Schweitzer et al.

(10) Patent No.: US 7,333,842 B2
(45) Date of Patent: Feb. 19, 2008

(54) METHOD FOR THE SPECTROSCOPIC DETERMINATION OF THE OXYGEN SATURATION OF BLOOD IN THE PRESENCE OF OPTICAL DISTURBANCE VARIABLES

(75) Inventors: Dietrich Schweitzer, Neustadt/Orla (DE); Martin Hammer, Jena (DE); Eike Thamm, Jena/Maua (DE)

(73) Assignee: Carl Ziess Mesitec AG, Jena (DE)

( * ) Notice: Subject to any disclaimer, the term of this patent is extended or adjusted under 35 U.S.C. 154(b) by 318 days.

(21) Appl. No.: 10/511,483

(22) PCT Filed: Apr. 17, 2003

(86) PCT No.: PCT/EP03/04024

§ 371 (c)(1),
(2), (4) Date: Sep. 7, 2005

(87) PCT Pub. No.: WO03/086193

PCT Pub. Date: Oct. 23, 2003

(65) Prior Publication Data

US 2006/0063994 A1   Mar. 23, 2006

(30) Foreign Application Priority Data

Apr. 17, 2002   (DE) ................................ 102 17 543

(51) Int. Cl.
*A61B 5/00* (2006.01)
(52) U.S. Cl. ...................................... 600/336; 600/323
(58) Field of Classification Search ................ 600/310, 600/322, 323, 336
See application file for complete search history.

(56) References Cited

U.S. PATENT DOCUMENTS 4,253,744 A   3/1981   Sawa
(Continued)

FOREIGN PATENT DOCUMENTS

DE   32 45 939   6/1984
(Continued)

OTHER PUBLICATIONS

J. Opt. Soc. Amer. 60, 1970, pp. 1084-1093 :Absorption and multiple scattering by biological suspension V. Twersky.

(Continued)

*Primary Examiner*—Eric F Winakur
(74) *Attorney, Agent, or Firm*—Reed Smith, LLP

(57) ABSTRACT

The invention is directed to a method for the spectrometric determination of the oxygen saturation of blood in the presence of optical disturbance variables in which transmission measurements and reflection measurements are carried out in at least two wavelengths that are isosbestic for hemoglobin and oxyhemoglobin, and at least one other wavelength at which the extinction of hemoglobin and oxyhemoglobin differ. Corresponding auxiliary functions are defined in the measurement spectrum (M) and in the reference spectra of hemoglobin and oxyhemoglobin, at least two of the measurement values or two of the reference values for the isosbestic wavelengths lying on this auxiliary function. A corrected measurement spectrum (M") is generated by the two auxiliary functions. The oxygen saturation is determined by comparing the changed data of this corrected measurement spectrum (M") with the data of the reference spectra at the other wavelength.

3 Claims, 2 Drawing Sheets

U.S. PATENT DOCUMENTS

| | | | |
|---|---|---|---|
| 4,305,398 A | 12/1981 | Sawa | |
| 4,485,820 A | 12/1984 | Flower | |
| 5,119,814 A | 6/1992 | Minnich | |
| 5,308,919 A | 5/1994 | Minnich | |
| 5,318,022 A | 6/1994 | Taboada et al. | |
| 5,776,060 A | 7/1998 | Smith et al. | |
| 5,935,076 A | 8/1999 | Smith et al. | |
| 6,501,974 B2* | 12/2002 | Huiku | 600/323 |
| 6,711,425 B1* | 3/2004 | Reuss | 600/323 |

FOREIGN PATENT DOCUMENTS

| | | |
|---|---|---|
| DE | 44 33 827 | 3/1996 |
| DE | 199 20 157 | 11/2000 |
| WO | WO 00/09004 | 2/2000 |

OTHER PUBLICATIONS

Appl. Opt. 39, 2000, pp. 1183-1193 "Effects of multiple light paths in retinal vessel oximetry" Smith, et al.

J. Appl. Physiol. 38, 1975, pp. 315-320 "A new method for the measurement of percent oxyhemoglobin" Pittman RN, t al.

Appl. Opt. 27, 1988, pp. 1183-1193 "Noninvasive technique for oximetry of blood in retinal vessels" F.C. Delori.

IEEE Trans Biomed Eng. 48 (5), 2001, pp. 592-598 "Light paths in retinal oeymetry".

IEEE Trans Biomed Eng. 46, 1999, pp. 1454-1465 "In Vivo Measurement of the oxygen Saturation at the Normal Human Eye" Schweitzer, et al.

* cited by examiner

METHOD FOR THE SPECTROSCOPIC DETERMINATION OF THE OXYGEN SATURATION OF BLOOD IN THE PRESENCE OF OPTICAL DISTURBANCE VARIABLES

CROSS-REFERENCE TO RELATED APPLICATIONS

This application claims priority of International Application No. PCT/EP03/04024, filed Apr. 17, 2003, and German Application No. 102 17 543.8, filed Apr. 17, 2002, the complete disclosures of which are hereby incorporated by reference.

BACKGROUND OF THE INVENTION a) Field of the Invention

The invention is directed to a method for the spectrometric determination of the oxygen saturation of blood in the presence of optical disturbance variables such as those also presented by pigmented and light-scattering surrounding tissue and/or also the vascular wall itself. This problem of determining the oxygen saturation of blood while excluding as far as possible the influence of these factors affecting measurement accuracy occurs particularly in noninvasive, in-vivo or in-vitro examinations of blood vessels located in front of, behind, or in said pigmented and scattering tissue, for example, in the examination of blood vessels of the ocular fundus or other tissue areas in the body such as the skin and organs that are accessible by endoscopy.

b) Description of the Related Art

It is generally known that the absorption spectrum of the red blood pigment hemoglobin changes with oxygen saturation (e.g., van Assendelft, O. W., Spectrophotometry of heamoglobin derivatives, Assen: Royal Vangorcum, 1970). Accordingly, it is possible to determine the oxygen saturation of a hemoglobin sample by comparing the spectrum of the sample to the spectra of completely oxygenated and completely reduced hemoglobin.

Recent work in oxymetry in the ocular fundus using the Lambert-Beerschen law, i.e., taking only absorption into account, has been published by Smith et al. and others (Smith, M. H., Denninghoff, K. R., Lompado, A., Hillman, L. W., Effect of multiple light paths in retinal vessel oxymetry, Appl. Opt. 39, 2000, 1183-1193). Numerous patented arrangements and methods are based on this principle (e.g., U.S. Pat. No. 4,485,820; U.S. Pat. No. 5,119,814; U.S. Pat. No. 5,308,919; U.S. Pat. No. 4,253,744; U.S. Pat. No. 4,305,398; U.S. Pat. No. 5,776,060; U.S. Pat. No. 5,935,076; DE 199 20 157 A1; U.S. Pat. No. 5,318,022).

However, the hemoglobin does not exist in isolation in in-vivo measurement, but is enclosed in the erythrocytes. The scattering of light on the erythrocytes has a considerable influence on the extinction spectrum of the blood. However, based on the findings of the multiple scattering theory of Twersky (Twersky, V., Absorption and multiple scattering by biological suspensions, J. Opt. Soc. Amer. 60, 1970, 1084-1093), the influences of scattering and absorption can be separated. On this basis, Pittman and Duling describe a method for determining the oxygen saturation in whole blood from measurements taken in transmission at a wavelength of 555 nm and at isosbestic points at 522 nm and 546 nm (Pittman, R. N., Duling, B. R., A new method for the measurement of percent oxyhemoglobin, J. Appl. Physiol., 38, 1975, 315-320). This method has been used by Delori to determine oxygen saturation in retinal vessels (Delori, F. C., Noninvasive technique of oximetry of blood in retinal vessels, Appl. Opt. 27, 1988, 1113-1125).

However, investigations by Hammer at al. (Hammer, M., Leistritz, S., Leistritz, L., Schweitzer, D., Light paths in retinal vessel oxymetry, IEEE Trans Biomed Eng 48 (5), 2001, 592-8) show that the reflection spectra measured on retinal vessels are influenced not only by the absorption of the hemoglobin and the scattering in the blood and in the tissue surrounding the vessels, but also by the melanin located in the retinal pigment epithelium and in the choroid. This is also true of vessels in the skin or other pigmented organs.

Correcting falsification of the hemoglobin spectra by means of other chromophores and correction for spectroscopic oxymetry have been attempted in previous literature by scaling the spectra measured on a vessel to measurements next to the vessel (e.g., DE 199 20 157 A1; U.S. Pat. No. 5,935,076; Delori, F. C., Noninvasive technique for oximetry of blood in retinal vessels, Appl. Opt. 27, 1988, 113-1125; Schweitzer, D., Hammer, M., Kraft, J., Thamm, E., Königsdörffer, E., Strobel, J., In Vivo Measurement of the Oxygen Saturation at the Normal Human Eye, IEEE Trans. Biomed. Eng. 46, 1999, 1454-1465). However, this approach does not take into account the extremely complicated relationships (Hammer, M., Leistritz, S., Leistritz, L., Schweitzer, D., Light paths in retinal vessel oxymetry, IEEE Trans Biomed Eng 48 (5), 2001, 592-8) of the beam propagation in the blood vessel and the tissue surrounding it.

The exact light propagation in the biological tissue cannot always be fully described physically. Even efforts to recreate these processes for eliminating disturbances in the most comprehensive and realistic manner possible (DE 199 20 157 A1) and to model the optics of the living or dead biological tissue surrounding the blood vessel (DE 44 33 827 A1) have not led to more exact measurements than the methods mentioned above, which are already relatively time-consuming and require intensive computation. In view of this, the methods are only conditionally suitable especially for routine examinations and screening examinations. In particular, the determination of oxygen saturation at every point of a two-dimensional, graphic recording, which is important for clinical practice, requires a method that is fast on the one hand and that compensates for optical and spectrometric disturbances due to the tissue environment on the other hand.

OBJECT AND SUMMARY OF THE INVENTION

Therefore, it is the primary object of the invention to determine the oxygen saturation with high accuracy by a method which is as simple and as fast as possible.

In order to meet the above-stated object, spectral measurements are generated by transmission measurement and reflection measurement in a measurement spectrum at wavelengths that are isosbestic for hemoglobin and oxyhemoglobin and at least one other measurement value is generated at a wavelength at which the reference values of hemoglobin and oxyhemoglobin differ, and these measurements are compared with known reference values of the reference spectra of hemoglobin and oxyhemoglobin in that:

a) at least two said spectral measurement values ($M_{i1}$, $M_{i2}$) at wavelengths ($\lambda_{i1}$, $\lambda_{i2}$) that are isosbestic for hemoglobin and oxyhemoglobin and at least the other measurement value ($M_a$) at a wavelength ($\lambda_a$) at which the reference values of hemoglobin and oxyhemoglobin differ as far as possible in the reference spectra are detected in the measurement spectrum, wherein an auxiliary function ($F_H$) is generated at least from two of the measurement values ($M_{i1}$, $M_{i2}$) for isosbestic wavelengths ($\lambda_{i1}$, $\lambda_{i2}$), b) a reference function ($F_R$) is generated in the reference spectra from the reference values ($R_{i1}$, $R_{i2}$) corresponding to the at least two measurement values ($M_{i1}$, $M_{i2}$) determined in the measurement spectrum for the same isosbestic wavelengths ($\lambda_{i1}$, $\lambda_{i2}$) of hemoglobin and oxyhemoglobin, which reference function ($F_R$) is of the same type, c) a correction function ($F_K$) is generated from the auxiliary function ($F_H$) of the measurement spectrum in which said at least two measurement values ($M_{i1}$, $M_{i2}$) lie for isosbestic wavelengths ($\lambda_{i1}$, $\lambda_{i2}$) and from the reference function ($F_R$) of the reference spectra in which the at least two reference values ($R_{i1}$, $R_{i2}$) corresponding to the at least two measurement values ($M_{i1}$, $M_{i2}$) lie, and a corrected auxiliary function ($F_{Hk}$) identical to the reference function ($F_R$) in the reference spectra is generated in a corrected measurement spectrum by means of this correction function ($F_K$), and d) the oxygen saturation of the blood is determined from the other measurement value ($M_a''$) converted to the corrected auxiliary function ($F_{Hk}$) of the corrected measurement spectrum in relation to the reference values for hemoglobin and oxyhemoglobin at this wavelength ($\lambda_a$).

It is advantageous when the spectral measurement values and reference data are determined logarithmically and the auxiliary function and reference function are formed by a straight line on which two of the measurement values or reference values lie for isosbestic wavelengths. The correction function formed from the linear auxiliary function and reference function can also give a linear corrected auxiliary function of the corrected measurement spectrum. A constant multiplier is applied to the rest of the spectral measurement values, i.e., the spectral measurement value for the third isosbestic wavelength and the other measurement value at a wavelength at which the reference values of hemoglobin and oxyhemoglobin differ as far as possible in the reference spectra. This constant multiplier is determined in such a way that the third isosbestic measurement value of the corrected measurement spectrum that is corrected by scaling conforms to the corresponding reference value of the reference spectra. In this specific case, the difference between the reference values for hemoglobin and oxyhemoglobin can be scaled linearly between 0 and 1. The oxygen saturation of the blood is determined in relation to this scale from the other measurement value that is converted to the corrected auxiliary function of the corrected measurement spectrum.

For purposes of a clear two-dimensional representation of the oxygen saturation of the blood, four monochromatic individual images are generated at said wavelengths and the oxygen saturation is determined for each image point.

Surprisingly, it has been shown that in comparison with the examination methods mentioned in the introduction, the oxygen saturation of the blood can be determined by the proposed method with the same accuracy but with substantially less effort (minimally, four measurement values are required) for measurement, calculation and evaluation. The method makes possible a two-dimensional, spatially dependent representation of the measurements allowing a manageable and fast evaluation. Only a few measurement values are required and only linear transformations are used. With these advantages of low expenditure and time-efficient measurement evaluation, the proposed method is also suitable for screening examinations as well as for routine and early detection examinations.

The invention will be described more fully in the following with reference to an embodiment example shown in the drawing.

DESCRIPTION OF THE PREFERRED EMBODIMENTS

Figure 1:
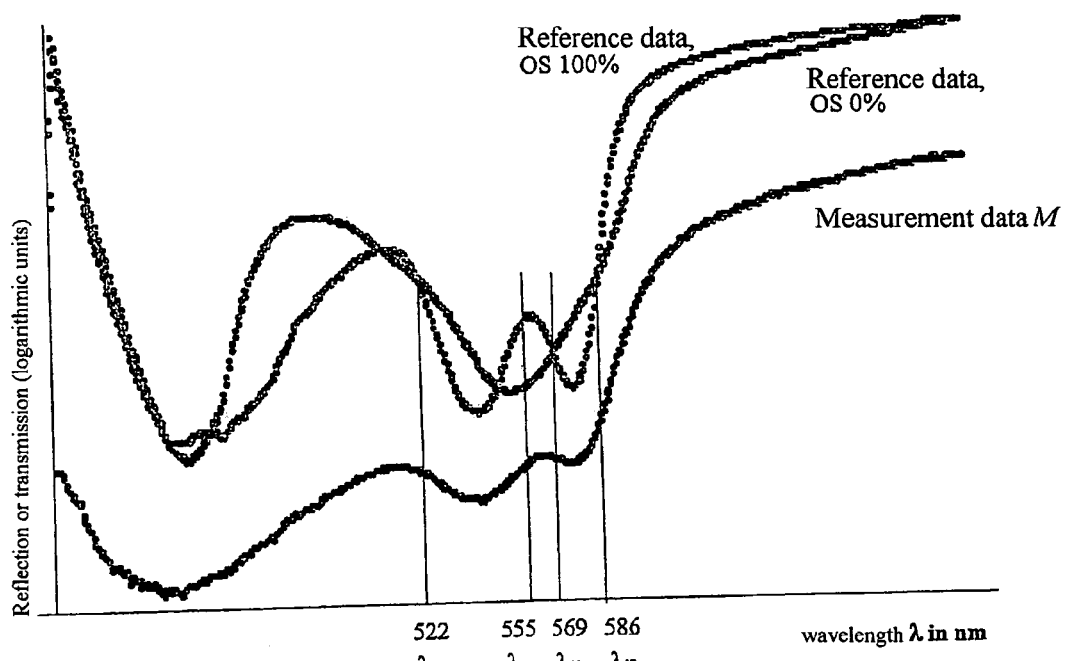
FIG. 1 is a graph showing measurement values and reference values in logarithmic form in the wavelength range between 400 nm and 700 nm, including three isosbestic wavelengths $\lambda_{i1}$=522 nm, $\lambda_{i2}$=586 nm, $\lambda_{i3}$=569 nm and the other wavelength $\lambda_a$=555 nm.

The reflection or transmission of tissue at a point or with spatial resolution in an image is measured at three isosbestic wavelengths $\lambda_{i1}$, $\lambda_{i2}$ and $\lambda_{i3}$ ($\lambda_{i1}$=522 nm, $\lambda_{i2}$=586 nm, $\lambda_{i3}$=569 nm) as measurement data $M_{i1}$, $M_{i2}$ and $M_{i3}$ and at a different wavelength $\lambda_a$ (555 nm), at which the absorption coefficients of oxygenated and reduced hemoglobin differ, as measurement value $M_a$ and is compared with the reflection or transmission of hemoglobin or whole blood with oxygen saturations of 0% and 100%, respectively, at these wavelengths (reference data $R_1$, $R_2$, $R_3$, $R_a^{0\%}$ and $R_a^{100\%}$) according to the following method:

1. All measurement data and reference data are logarithmized. FIG. 1 shows the measurement data and reference data represented logarithmically, which are, in this example, the reflection of a retinal vein (measurement data) and the transmission of a layer of whole blood with a thickness of 0.1 mm (reference data). For the sake of clarity, the complete spectra between 400 nm and 700 nm are shown. The wavelengths $\lambda_{i1}$=522 nm, $\lambda_{i2}$=586 nm, $\lambda_{i3}$=569 nm and $\lambda_a$=555 nm used in this example are shown.

2. A linear auxiliary function $F_H$ of the wavelength is calculated in the measurement spectra such that its values at the isosbestic wavelengths $\lambda_{i1}$ and $\lambda_{i2}$ agree with the measurement data $M_{i1}$ and $M_{i2}$ at these wavelengths.

3. A linear reference function $F_R$ of the wavelength is calculated in the reference spectra in such a way that its values at the isosbestic wavelengths $\lambda_{i1}$ and $\lambda_{i2}$ agree with the reference data $R_{i1}$, $R_{i2}$ at these wavelengths.

4. The measurement data are corrected additively at each wavelength by the difference of the linear functions $F_H$ and $F_R$ in such a way that at the isosbestic wavelengths $\lambda_{i1}$ and $\lambda_{i2}$ they agree with the reference data: $M'_\lambda = M_\lambda + F_R - F_H$.

Figure 2:
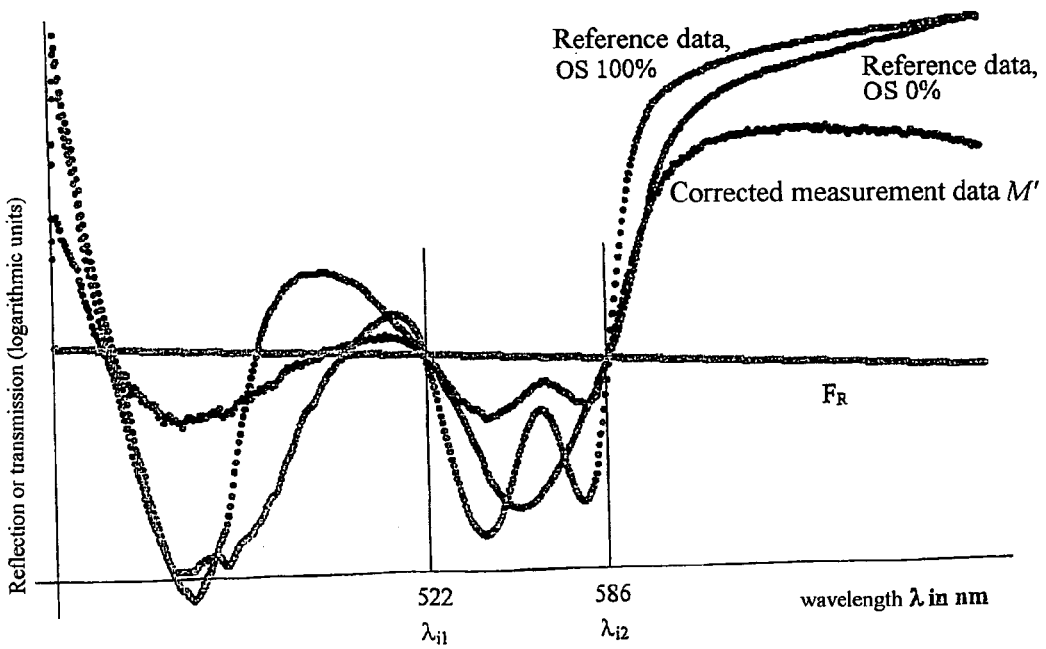
FIG. 2 is a graph with spectral reference values according to FIG. 1 showing linear reference function $F_R$ and corrected measurement values M'.

FIG. 2 again shows the reference data, the linear reference function $F_R$ of the wavelength and the corrected measurement data M'. This correction compensates for extinctions which exist in addition to the absorption of the hemoglobin and whose spectra in the wavelength range of 522 nm to 586 nm can be assumed or approximated as linear in the logarithmic scale. The embodiment example under consideration concerns absorptions of melanin and the anterior optical media and the scattering in the blood and in the surrounding tissue.

5. The corrected measurement data M' are scaled by a factor of less than or greater than 1 around the linear reference function $F_R$ in such a way that they agree with the reference value $R_{i3}$ at the isosbestic wavelength $\lambda_{i3}$:

$$M''_\lambda = F_R(\lambda) + \frac{(M'_\lambda - F_R(\lambda))(R_{i3} - F_R(\lambda_3))}{M'_{i3} - F_R(\lambda_3)}. \qquad 5$$

Figure 3:
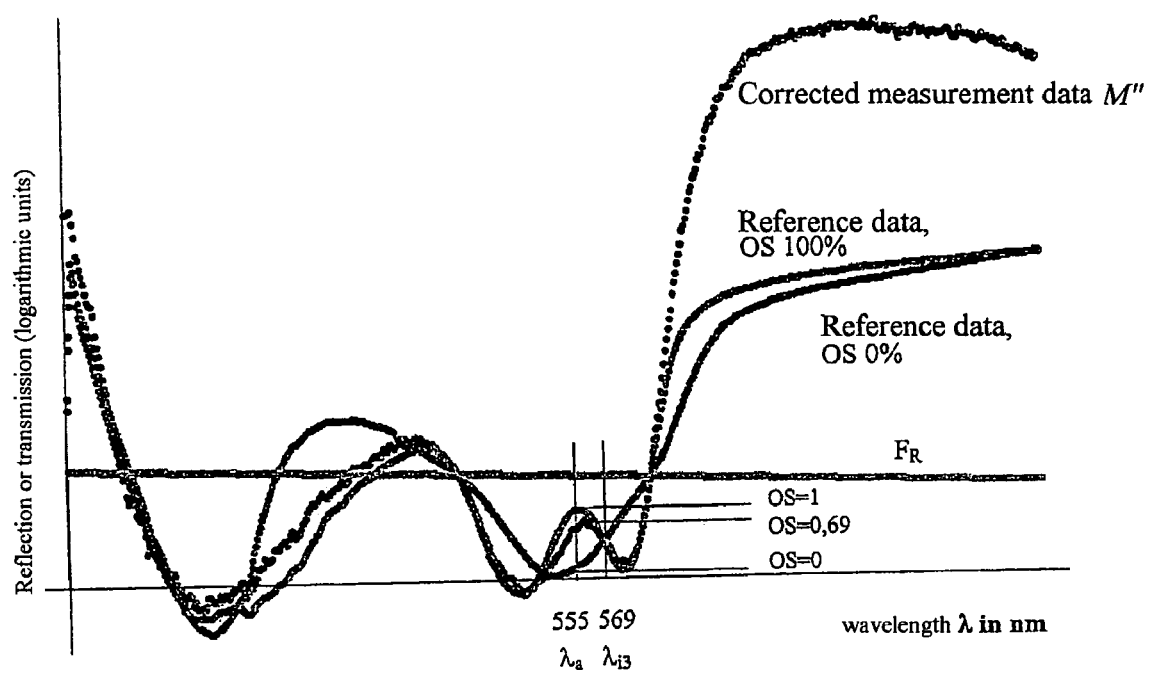
FIG. 3 is a graph with spectral reference values according to FIG. 1 showing linear reference function $F_R$ with corrected measurement values M" and with scaling for reading off oxygen saturation.

FIG. 3 shows the spread (or scaling) of the corrected measurement data M' resulting in M" around the linear reference function $F_R$ which is carried out in such a way that corrected measurement data and reference data agree at the isosbestic wavelength $\lambda_{i3}$ (569 nm). This correction compensates for different absolute values of the measurement data and reference data that occur due to different illumination conditions and measurement conditions.

6. The position of $M''_a$ on a scale contained linearly between $R_a^{0\%}$ and $R_a^{100\%}$ indicates the oxygen saturation OS:

$$OS = \frac{M''_a - R_a^{0\%}}{R_a^{100\%} - R_a^{0\%}}.$$

The scaled readout of the oxygen saturation (OS) between the values 0 and 1 is likewise shown in FIG. 3. The oxygen saturation OS in the embodiment example is 0.69.

While the foregoing description and drawings represent the present invention, it will be obvious to those skilled in the art that various changes may be made therein without departing from the true spirit and scope of the present invention.

Reference Numbers
M—measurement data
M'—measurement data corrected by the addition of the corrected auxiliary function
M"—measurement data M' corrected by applying a factor
$F_R$—reference function
OS—oxygen saturation
$\lambda$—wavelength

What is claimed is:

1. A method for determining the oxygen saturation of blood in the presence of optical disturbance variables, particularly due to a biological tissue surrounding the blood vessel and/or the blood and/or the blood vessel itself comprising the steps of:
generating spectral measurements ($M_i$) by transmission measurement and reflection measurement in a measurement spectrum at wavelengths that are isosbestic for hemoglobin (Hb) and oxyhemoglobin ($HbO_2$);
generating at least one other measurement value ($M_a$) at a wavelength at which the reference values of hemoglobin and oxyhemoglobin differ; and
comparing these measurements with known reference values of the reference spectra of hemoglobin and oxyhemoglobin; and further comprising the steps of:
a) detecting at least two said spectral measurement values ($M_{i1}$, $M_{i2}$) at wavelengths ($\lambda_{i1}$, $\lambda_{i2}$) that are isosbestic for hemoglobin and oxyhemoglobin and at least the other measurement value ($M_a$) at a wavelength ($\lambda_a$) at which the reference values of hemoglobin and oxyhemoglobin differ as far as possible in the reference spectra in the measurement spectrum, wherein an auxiliary function ($F_H$) is generated at least from two of the measurement values ($M_{i1}$, $M_{i2}$) for isosbestic wavelengths ($\lambda_{i1}$, $\lambda_{i2}$);
b) generating a reference function ($F_R$) in the reference spectra from the reference values ($R_{i1}$, $R_{i2}$) corresponding to the at least two measurement values ($M_{i1}$, $M_{i2}$) determined in the measurement spectrum for the same isosbestic wavelengths ($\lambda_{i1}$, $\lambda_{i2}$) of hemoglobin and oxyhemoglobin, which reference function ($F_R$) is of the same type;
c) generating a correction function ($F_K$) from the auxiliary function ($F_H$) of the measurement spectrum in which said at least two measurement values ($M_{i1}$, $M_{i2}$) lie for isosbestic wavelengths ($\lambda_{i1}$, $\lambda_{i2}$) and from the reference function ($F_R$) of the reference spectra in which the at least two reference values ($R_{i1}$, $R_{i2}$) corresponding to the at least two measurement values ($M_{i1}$, $M_{i2}$) lie, and generating a corrected auxiliary function ($F_{Hk}$) identical to the reference function ($F_R$) in the reference spectra in a corrected measurement spectrum by this correction function ($F_K$); and
d) determining the oxygen saturation of the blood from the other measurement value ($M_a$") converted to the corrected auxiliary function ($F_{Hk}$) of the corrected measurement spectrum in relation to the reference values for hemoglobin and oxyhemoglobin at this wavelength ($\lambda_a$).

2. The method according to claim 1, including the steps of:
a) logarithmically determining three said spectral measurement values ($M_{i1}$, $M_{i2}$, $M_{i3}$) at wavelengths ($\lambda_{i1}$, $\lambda_{i2}$, $\lambda_{i3}$) that are isosbestic for hemoglobin and oxyhemoglobin and another measurement value ($M_a$) at a wavelength ($\lambda_a$) at which the reference values of hemoglobin and oxyhemoglobin differ as far as possible in the reference spectra, wherein a linear auxiliary function ($F_H$) is generated from two logarithmic measurement values ($M_{i1}$, $M_{i2}$) for isosbestic wavelengths ($\lambda_{i1}$, $\lambda_{i2}$);
b) generating a linear reference function ($F_R$) in the reference spectra from the reference values ($R_{i1}$, $R_{i2}$) corresponding to the measurement values ($M_{i1}$, $M_{i2}$) determined in the measurement spectrum for the same isosbestic wavelengths ($\lambda_{i1}$, $\lambda_{i2}$) of hemoglobin and oxyhemoglobin;
c) generating a linear correction function ($F_K$) from the auxiliary function ($F_H$) of the measurement spectrum and from the reference function ($F_R$) of the reference spectra, and generating a likewise linear corrected auxiliary function ($F_{Hk}$) identical to the linear reference function ($F_R$) in the reference spectra in the corrected measurement spectrum by this linear correction function ($F_K$);
d) applying a constant multiplier to the rest of the corrected spectral measurement values, i.e., the third spectral measurement value ($M_{i3}'$) at a wavelength ($\lambda_{i3}$) that is isosbestic for hemoglobin and oxyhemoglobin and the other measurement value at a wavelength ($\lambda_a$) at which the reference values of hemoglobin and oxyhemoglobin differ as far as possible in the reference spectra, this constant multiplier being determined in such a way that the third spectral measurement value ($M_{i3}'$) of the corrected measurement spectrum that is corrected in this way conforms to the corresponding reference value of the reference spectra; and
e) reading off the oxygen saturation of the blood at the other measurement value ($M_a$") that is converted to the corrected auxiliary function ($F_{Hk}$) of the corrected measurement spectrum on a scale from 0 to 1 contained by the reference values for hemoglobin and oxyhemoglobin at this wavelength ($\lambda_a$).

3. The method according to claim 1, wherein, for purposes of a two-dimensional representation of the oxygen saturation of the blood, four monochromatic individual images of the spectral measurement values ($M_i$, $M_a$) are generated, and wherein the oxygen saturation is determined according to steps a) to d) for each image point.

\* \* \* \* \*

UNITED STATES PATENT AND TRADEMARK OFFICE
CERTIFICATE OF CORRECTION

PATENT NO.         : 7,333,842 B2
APPLICATION NO.    : 10/511483
DATED              : February 19, 2008
INVENTOR(S)        : Dietrich Schweitzer et al.

It is certified that error appears in the above-identified patent and that said Letters Patent is hereby corrected as shown below:

TITLE PAGE

The assignee's name should read as follows:

[73]   Carl Zeiss Meditec AG, Jena (DE)

Signed and Sealed this

Eighth Day of July, 2008

JON W. DUDAS
*Director of the United States Patent and Trademark Office*